US012661075B2

(12) United States Patent
Hofmann et al.

(10) Patent No.: US 12,661,075 B2
(45) Date of Patent: Jun. 23, 2026

(54) METHOD FOR PROVIDING ADAPTED 4D CT DATA

(71) Applicant: Siemens Healthineers AG, Forchheim (DE)

(72) Inventors: Christian Hofmann, Erlangen (DE); Matthias Baer-Beck, Spardorf (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 57 days.

(21) Appl. No.: 18/755,856

(22) Filed: Jun. 27, 2024

(65) Prior Publication Data

US 2025/0000464 A1     Jan. 2, 2025

(30) Foreign Application Priority Data

Jun. 30, 2023     (EP) ..................................... 23182866

(51) Int. Cl.
| *A61B 6/03* | (2006.01) |
| *A61B 6/00* | (2006.01) |
| *A61B 6/50* | (2024.01) |
| *G16H 20/40* | (2018.01) |

(52) U.S. Cl.
CPC .............. *A61B 6/032* (2013.01); *A61B 6/488* (2013.01); *A61B 6/50* (2013.01); *G16H 20/40* (2018.01)

(58) Field of Classification Search
CPC ........... A61B 6/032; A61B 6/488; A61B 6/50; G16H 20/40
See application file for complete search history.

(56) References Cited

U.S. PATENT DOCUMENTS

| 2008/0260095 A1 | 10/2008 | Sukovic et al. |
| 2013/0272593 A1 | 10/2013 | Lee et al. |
| 2014/0275704 A1* | 9/2014 | Zhang .................. A61N 5/1067 |
| | | 600/1 |

(Continued)

FOREIGN PATENT DOCUMENTS

| CN | 103380441 A | 10/2013 |
| CN | 115251963 A | 11/2022 |
| WO | WO 2022036442 A1 | 2/2022 |

OTHER PUBLICATIONS

Extended European Search Report for European Application No. 23182866.6 mailed Dec. 19, 2023.

(Continued)

*Primary Examiner* — Hugh Maupin
(74) *Attorney, Agent, or Firm* — Harness, Dickey & Pierce, P.L.C.

(57)     ABSTRACT

One or more example embodiments relates to a computer-implemented method for providing adapted 4D C T data, the method comprising receiving initial 4D CT data, the initial 4D CT data corresponding to a first 4D CT scan, the first 4D CT scan relating to an anatomical structure on a first examination date; receiving supplementary 4D CT data, the supplementary 4D CT data corresponding to a partial 4D CT scan, the partial 4D CT scan relating to the anatomical structure on a second examination date; calculating the adapted 4D CT data based on the initial 4D CT data and the supplementary 4D CT data, the adapted 4D CT data corresponding to a second 4D CT scan, the second 4D CT scan relating to the anatomical structure on the second examination date; and providing the adapted 4D CT data.

20 Claims, 3 Drawing Sheets

(56)         References Cited

U.S. PATENT DOCUMENTS

| | | | |
|---|---|---|---|
| 2015/0005659 A1* | 1/2015 | Masumoto ............. | A61B 6/032 |
| | | | 600/538 |
| 2016/0279444 A1 | 9/2016 | Schlosser | |
| 2018/0345042 A1 | 12/2018 | Voronenko et al. | |
| 2019/0231296 A1 | 8/2019 | Jackson et al. | |
| 2020/0160972 A1* | 5/2020 | Bériault ................ | G06N 3/045 |
| 2021/0248790 A1* | 8/2021 | Dang ................... | G06T 11/006 |
| 2022/0398717 A1* | 12/2022 | Hébert .................... | G06N 3/09 |
| 2023/0302297 A1 | 9/2023 | Lachaine et al. | |
| 2023/0338749 A1 | 10/2023 | Hofmann et al. | |

OTHER PUBLICATIONS

European Communication under Rule 71(3) for European Application No. 23182866.6 mailed Feb. 18, 2025.

Werner R. et al.: "Intelligent 4D CT sequence scanning (i4DCT): Concept and performance evaluation", Medical Physics, 47(6)2020, 3462-3474.

Siemens Healthineers "4D CT cookbook 2.1", A guide to 4D CT imaging in RT, 2020, 28 pages.

Werner Rene et al.;.: "Intelligent 4D CT sequence scanning (i4DCT): First scanner prototype implementation and phantom measurements of automated breathing signal-guided 4D CT", Med.Phys. 47 (6), Jun. 2020, pp. 2408-2412.

* cited by examiner

METHOD FOR PROVIDING ADAPTED 4D CT DATA

CROSS-REFERENCE TO RELATED APPLICATION(S)

The present application claims priority under 35 U.S.C. § 119 to European Patent Application No. 23182866.6, filed Jun. 30, 2023, the entire contents of which is incorporated herein by reference.

FIELD

One or more example embodiments relates to a computer-implemented method for providing adapted 4D CT data. At least another example embodiment relates to a data processing system, to a computer program product, to a computer-readable storage medium, to a medical imaging device and to a radiation treatment planning system.

RELATED ART

Cancer treatment, in particular lung cancer treatment, is constantly evolving due to technological advances in the delivery of radiation therapy. Adaptive radiation therapy (ART) allows for modification of a treatment plan with the goal of improving the dose distribution to a patient due to anatomic and/or physiologic deviations from the initial simulation. Cancer radiation treatment planning may be based on 4D CT data (four-dimensional computed tomography data). A 4D CT simulation may be applied onto the 4D CT data, generating a snapshot of the tumor size, shape, and position relative to normal tissue, which is used for the creation of an internal gross tumor volume (IGTV) or internal target volume (ITV). While the technologies to treat these tumors allow for highly conformal dose distributions, the complex geometric uncertainties involved in lung cancer treatment planning require large safety margins to create the planning target volume (PTV), which may hamper dose escalation.

Additionally, since treatment cycles and the overall duration of the treatment are typically quite long in radiation therapy it can happen that there are weeks between the acquisition of the planning images and the actual treatment. This constitutes the risk of poor tumor coverage and more severe off-target effects. ART addresses these weaknesses by enabling periodic changes to the treatment plan. 4D CT image acquisition however may pose a non-neglectable dose burden for the patient, for example, in the region of 30 to 60 mGy. Therefore, adaptive planning for moving tumors in liver and lung poses a challenge of additional dose burden. This restricts clinicians to follow the approach of a "plan of the day" wherein the initial treatment plan is adapted just before each treatment to improve accuracy.

SUMMARY

An underlying technical problem is to facilitate an adaptive treatment planning in medical radiology that is improved in particular with regard to radiation dose and image quality. This problem is solved by the subject matter of the independent claims. The dependent claims are related to further aspects. Independent of the grammatical term usage, individuals with male, female or other gender identities are included within the term.

One or more example embodiments relates to a computer-implemented method for providing adapted 4D CT data, the method comprising:

Receiving initial 4D CT data, the initial 4D CT data corresponding to a first 4D CT scan, the first 4D CT scan relating to an anatomical structure on a first examination date, Receiving supplementary 4D CT data, the supplementary 4D CT data corresponding to a partial 4D CT scan, the partial 4D CT scan relating to the anatomical structure on a second examination date, Calculating the adapted 4D CT data based on the initial 4D CT data and the supplementary 4D CT data, the adapted 4D CT data corresponding to a second 4D CT scan, the second 4D CT scan relating to the anatomical structure on the second examination date, Providing the adapted 4D CT data.

BRIEF DESCRIPTION OF THE DRAWINGS

One or more example embodiments will be illustrated below with reference to the accompanying figures. The illustration in the figures is schematic and highly simplified and not necessarily to scale.

DETAILED DESCRIPTION

Figure 1:
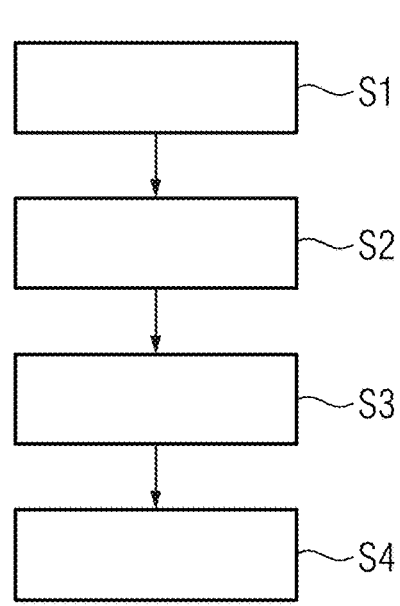
FIG. 1 shows a flow chart for a computer-implemented method for providing adapted 4D CT data.

An anatomical structure may be an anatomical structure of a patient. The anatomical structure may be, for example, an organ, in particular a lung or a liver. The anatomical structure may comprise a lesion, for example a tumor.

4D CT data may relate to three dimensions of space and one dimension of time. The dimension of time may relate, in particular, to a breathing signal and/or a sequence of breathing phases. The first 4D CT scan may be a first full quality 4D CT scan. Compared to the first 4D CT scan, the partial 4D CT scan exposes the anatomical structure to less radiation dose, thereby compromising on image quality, image resolution, time resolution and/or scan range. In particular, the initial 4D CT data may cover at least one 4D sample point that is not covered by the supplementary 4D CT data.

An initial treatment plan may be calculated based on the initial 4D CT data. For example, a first representation of the anatomical structure may be calculated based on the initial 4D CT data, the first representation of the anatomical structure relating to the anatomical structure on the first examination date. In particular, first information relating to a size and/or motion of a tumor of the anatomical structure and/or to an anatomical and/or morphological situation in the patient may be calculated based on the initial 4D CT data. The initial treatment plan may be calculated, for example, based on the first representation and/or based on the first information.

An adapted treatment plan may be calculated based on the adapted 4D CT data. For example, a second representation of the anatomical structure may be calculated based on the adapted 4D CT data, the second representation of the anatomical structure relating to the anatomical structure on the second examination date. In particular, second information relating to the size and/or motion of the tumor of the anatomical structure and/or to the anatomical and/or morphological situation in the patient may be calculated based on the adapted 4D CT data. The adapted treatment plan may be calculated, for example, based on the second representation and/or based on the second information.

To lower the dose burden for an adaptive replanning, in particular for an update of the treatment plan right before the actual treatment (to create a "plan of the day") or at defined time points during the treatment, the initial 4D CT data may be used as prior information and modified based on up-to-date information from the supplementary 4D CT data. The usage of prior information from the initial 4D CT data may help to reduce the dose burden of adaptive updates of the 4D CT planning data set during radiation treatment planning, in particular in the form of incremental replanning.

For example, the second 4D CT scan may be essentially equivalent to a repeat of the first 4D CT scan on the second examination date. In particular, the second examination date may be later in time than the first examination date. For example, the second examination date may occur at least two days after the first examination date, at least one week after the first examination date and/or at least one month after the first examination date.

The proposed method may enable a dose-reduced workflow for 4D CT imaging which would allow for an adaptive recalculation of treatment plans during different fractions of a treatment in order to adapt the radiation plan to changes during the treatment. The changes may relate, for example, to a tumor size, a tumor motion, a morphology and/or a situation of tissue surrounding the tumor.

Since there might be several weeks between the acquisition of the initial 4D CT data and the actual treatment such a method may help to significantly increase the quality, effectiveness and accuracy of radiation treatment planning while keeping the additional dose burden low.

A radiation dose may be reduced, in particular significantly reduced, for the partial 4D CT scan compared to the first 4D CT scan. In particular, the partial 4D CT may be dose-reduced with respect to the first 4D CT scan by an order of magnitude, for example to enable approaches like performing a 4D CT based adaptive replanning or even going into the direction of a "plan of the day". The radiation dose of the second 4D CT scan may be comparable, in particular essentially equivalent, in particular equivalent, to the radiation dose of the first 4D CT scan.

The radiation dose of the first 4D CT scan may be higher than 10 mGy, in particular higher than 30 mGy, and/or smaller than 100 mGy, in particular smaller than 60 mGy. The radiation dose of the partial 4D CT scan may be smaller than 50% of the radiation dose of the first 4D CT scan, in particular smaller than 25% of the radiation dose of the first 4D CT scan, in particular smaller than 10% of the radiation dose of the first 4D CT scan. The radiation dose of the second 4D CT scan may be higher than 50% of the radiation dose of the first 4D CT scan, in particular higher than 75% of the radiation dose of the first 4D CT scan, in particular equal to the radiation dose of the first 4D CT scan.

Since the adapted 4D CT data correspond to the second 4D CT scan, it is not required by the method to apply the second 4D CT scan to the anatomical region, neither explicitly nor implicitly. The second 4D CT scan may be understood as a fiction used for characterizing the adapted 4D CT data.

A scanned volume fraction of the anatomical structure may be reduced, in particular significantly reduced, for the partial 4D CT scan compared to the first 4D CT scan. Throughout this specification, significantly reduced may be understood as reduced by a factor of at least 2, in particular reduced by a factor of at least 4, for example reduced by a factor of at least 10. The scanned volume fraction of the second 4D CT scan may be comparable, in particular essentially equivalent, in particular equivalent, to the scanned volume fraction of the first 4D CT scan. To generate the supplementary 4D CT data, a partial 4D CT scan of only the most relevant regions, for example those regions that contain the tumor, may be done.

A scan range of the partial 4D CT scan may be selected based on the initial 4D CT data, the scan range of the partial 4D CT scan being reduced, in particular significantly reduced, compared to a scan range of the first 4D CT scan. The scan range of the second 4D CT scan may be comparable, in particular essentially equivalent, in particular equivalent, to the scan range of the first 4D CT scan. To reduce the volume fraction that is scanned and therefore irradiated during the partial 4D CT scan one possible way would be to reduce the scan range of the 4D CT scan and to adjust it so that only the region of tumor motion is irradiated during the scan.

An extent of an irradiation field along an x-ray fan direction may be reduced, in particular significantly reduced, for the partial 4D CT scan compared to the first 4D CT scan. The extent of the irradiation field along the x-ray fan direction of the second 4D CT scan may be comparable, in particular essentially equivalent, in particular equivalent, to the extent of the irradiation field along the x-ray fan direction of the first 4D CT scan. If the used CT scanner is capable of adjusting its irradiation field also along the fan direction this would be another source of possible radiation reduction potential. In this case the first 4D CT scan may be used in order to do a detruncation of the partial 4D CT scan.

Once the partial 4D CT scan with reduced irradiation range has been done it is proposed to combine the supplementary 4D CT data with the initial 4D CT data. Thereby the tumor region in the initial 4D CT data may be replaced and/or updated by the supplementary 4D CT data. To adjust the initial 4D CT data and the supplementary 4D CT data in the transition regions, a non-rigid registration or any other suited image registration algorithm can be used.

A scanned fraction of a breathing cycle may be reduced, in particular significantly reduced, for the partial 4D CT scan compared to the first 4D CT scan. The scanned fraction of the breathing cycle of the second 4D CT scan may be comparable, in particular essentially equivalent, in particular equivalent, to the scanned fraction of the breathing cycle of the first 4D CT scan. In particular, the breathing cycle may be the breathing cycle of the patient. For example, the partial 4D CT scan may be applied to a fraction of the breathing cycle, in particular only to the exhalation or to the inhalation phase, but to a scan range of the partial 4D CT scan that is equivalent to the scan range of the first 4D CT scan.

The adapted 4D CT data may be calculated based on the initial 4D CT data and the supplementary 4D CT data by applying an image registration, in particular a non-rigid transformation, from a given phase of the breathing cycle scanned during the first 4D CT scan to its corresponding phase in the part of the breathing cycle that was skipped during the partial 4D CT scan. Thereby the missing parts on the breathing cycle in the partial 4D CT scan, can be filled out to obtain the adapted 4D CT data covering the whole breathing cycle. Thereby, the image information regarding the missing phase is taken from the original full quality 4D CT. The breathing signal for the adapted 4D CT data can be either acquired in full during, before and/or after the partial 4D CT scan. Another option is to acquire a partial breathing signal covering only the scanned fraction of the breathing cycle of the partial scan and use it to calculate the missing part of the breathing signal, for example, based on the assumption, that an inhalation movement is essentially reverse to the exhalation movement.

The partial 4D CT scan may be a prospective phase selective 4D CT scan of a single phase of the breathing cycle. In particular, the prospective phase selective 4D CT scan may be a prospectively triggered phase selective 4D CT scan. In this case the 3D volume information would be taken from the supplementary 4D CT data while the information of the breathing motion would be taken from the initial 4D CT data.

A motion vector field of a breathing motion of the anatomical structure may be calculated based on the initial 4D CT data, wherein the adapted 4D CT data is calculated based on the motion vector field and the supplementary 4D CT data, in particular the supplementary 4D CT data for the single phase of the breathing cycle. The motion vector field of the breathing motion may be calculated based on the initial 4D CT data and used for calculating the adapted 4D CT data based on the supplementary 4D CT data resulting from the partial 4D CT scan of the single phase. By using the information from the initial 4D CT data the whole motion vector field of the breathing motion can be computed which allows to transform each phase into each other phase of the cycle.

An initial radiation treatment planning data regarding the anatomical structure may be calculated based on the initial 4D CT data and/or an adapted radiation treatment planning data regarding the anatomical structure may be calculated based on the adapted 4D CT data.

One or more example embodiments further relates to a computer program product or a computer-readable storage medium, comprising instructions which, when the instructions are executed by a computer, cause the computer to carry out the method according to one of the aspects of one or more example embodiments.

One or more example embodiments further relates to a data processing system, comprising a data interface and a processor, the data processing system being configured for carrying out the method according to one of the aspects of one or more example embodiments.

One or more example embodiments further relates to a medical imaging device, comprising the data processing system according to one of the aspects of one or more example embodiments and being configured for carrying out the first 4D CT scan relating to the anatomical structure to obtain the initial 4D CT data and/or for carrying out the partial 4D CT scan relating to the anatomical structure to obtain the supplementary 4D CT data.

The medical imaging device may be, for example, a computed tomography device and/or a cone beam CT device.

One or more example embodiments further relates to a radiation treatment planning system, comprising the data processing system according to one of the aspects of one or more example embodiments and being configured for providing the initial radiation treatment planning data regarding the anatomical structure and/or for providing the adapted radiation treatment planning data regarding the anatomical structure.

Any of the algorithms and/or models mentioned herein can be based on one or more of the following architectures: deep convolutional neural network, deep belief network, random forest, deep residual learning, deep reinforcement learning, recurrent neural network, Siamese network, generative adversarial network or auto-encoder.

The computer program product can be, for example, a computer program or comprise another element apart from the computer program. This other element can be hardware, for example a memory device, on which the computer program is stored, a hardware key for using the computer program and the like, and/or software, for example, a documentation or a software key for using the computer program. A computer-readable storage medium can be embodied as non-permanent main memory (e.g. random-access memory) or as permanent mass storage (e.g. hard disk, USB stick, SD card, solid state disk).

The data processing system can comprise, for example, at least one of a cloud-computing system, a distributed computing system, a computer network, a computer, a tablet computer, a smartphone or the like. The data processing system can comprise hardware and/or software. The hardware can be, for example, a processor system, a memory system and combinations thereof. The hardware can be configurable by the software and/or be operable by the software. Calculations for performing an action of a method may be carried out in the processor.

Data, in particular the initial 4D CT data and the supplementary 4D CT data, can be received, in particular received through a data interface, for example, by receiving a signal that carries the data and/or by reading the data from a computer memory and/or by a manual user input, for example, through a graphical user interface. Data, in particular the adapted 4D CT data and/or radiation treatment planning data, can be provided, in particular provided through a data interface for example, by transmitting a signal that carries the data and/or by writing the data into a computer memory and/or by displaying the data on a display.

In the context herein, the expression "based on" can in particular be understood as meaning "using, inter alia". In particular, wording according to which a first feature is calculated (or generated, determined etc.) based on a second feature does not preclude the possibility of the first feature being calculated (or generated, determined etc.) based on a third feature.

Reference is made to the fact that the described methods and the described systems are merely preferred example embodiments, and that example embodiments can be varied by a person skilled in the art, without departing from the scope as it is specified by the claims.

FIG. 1 shows a flow chart for a computer-implemented method for providing adapted 4D CT data.

Figure 2:
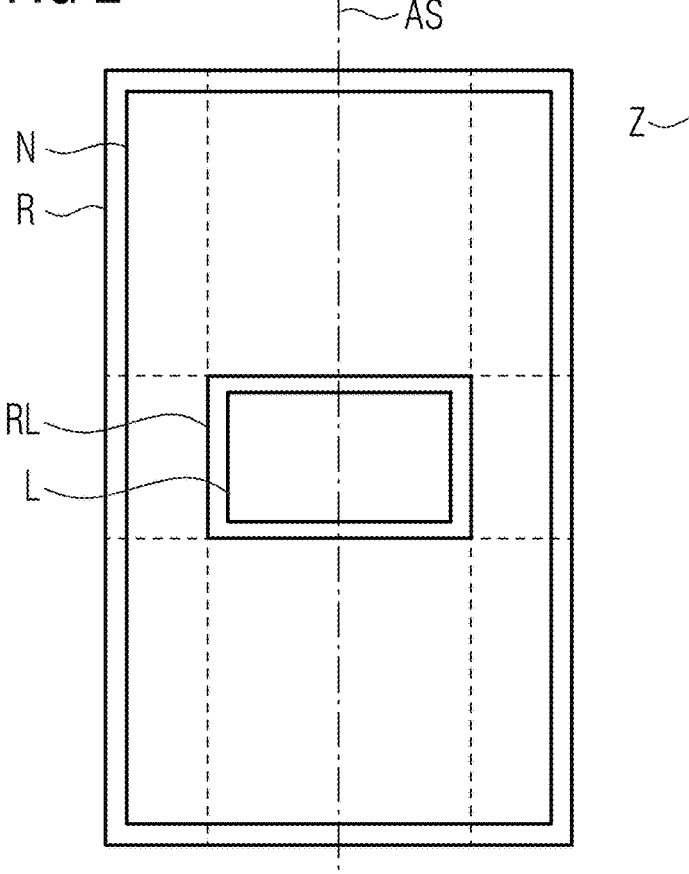
FIG. 2 shows an anatomical structure.

FIG. 2 shows the anatomical structure N comprising the lesion L. The irradiation field RL of the partial 4D CT scan is significantly reduced compared to the irradiation field R of the first 4D CT scan. The scan range of the first 4D CT scan is the extent of the irradiation field R along the scan direction Z. The scan range of the partial 4D CT scan is the extent of the irradiation field RL along the scan direction Z and significantly smaller than the scan range of the first 4D CT scan.

For the example shown in FIG. 2, a radiation dose is reduced for the partial 4D CT scan compared to the first 4D CT scan, a scanned volume fraction of the anatomical structure N is reduced for the partial 4D CT scan compared to the first 4D CT scan, a scan range of the partial 4D CT scan is reduced compared to a scan range of the first 4D CT scan and an extent of an irradiation field along an x-ray fan direction X is reduced for the partial 4D CT scan compared to the first 4D CT scan.

Figure 3:
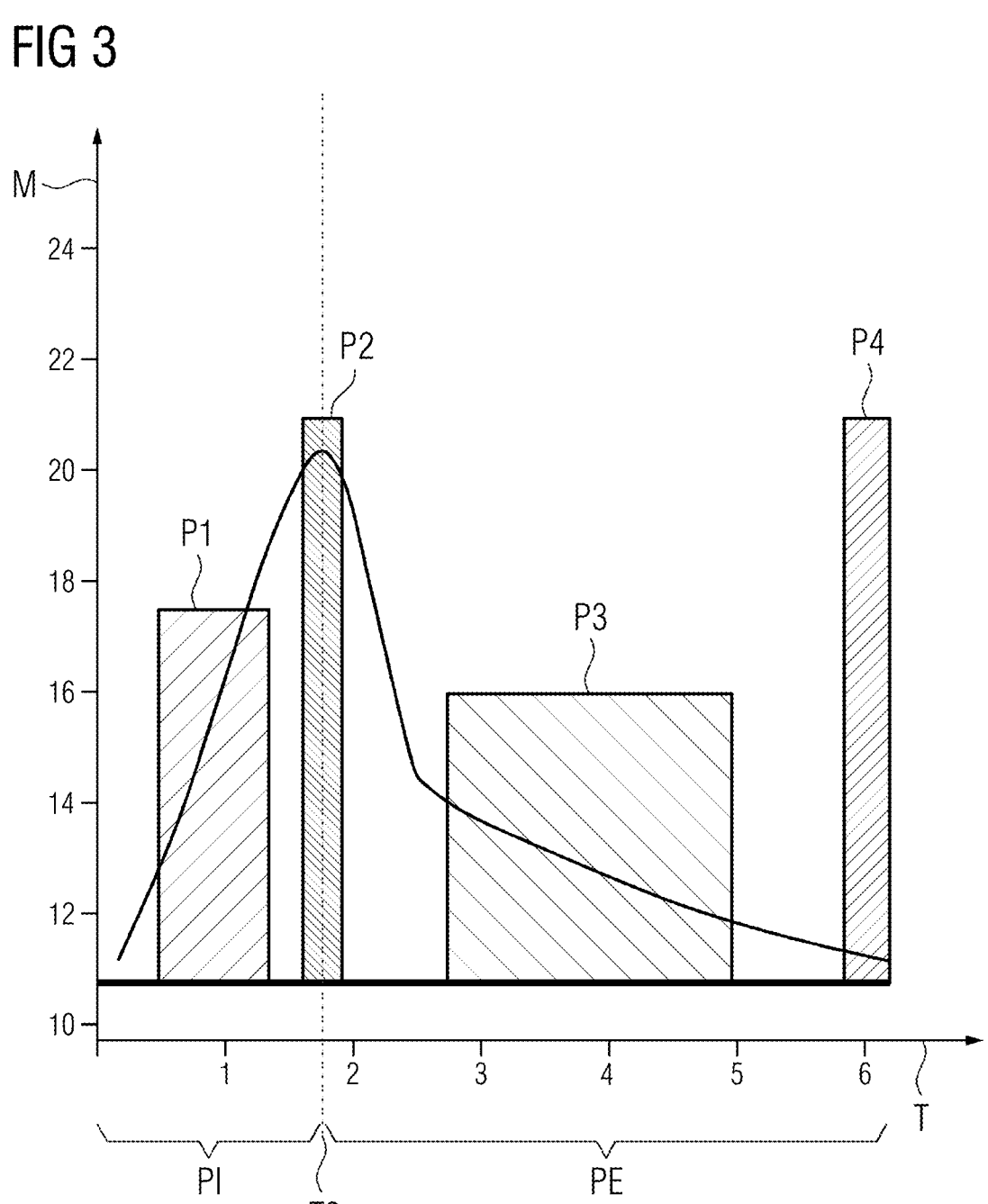
FIG. 3 shows a breathing cycle diagram.

FIG. 3 shows a breathing cycle diagram with the magnitude M over time T, covering the inhalation phase PI, the exhalation phase PE and the single phases P1, P2, P3 and P4. The prospective phase selective 4D CT scan may be, for example, triggered prospectively, to cover the single phase P2 maximum inhalation state at the timepoint T2. In this case, a scanned fraction of the breathing cycle is reduced for the partial 4D CT scan compared to the first 4D CT scan, the first 4D CT scan covering the whole breathing cycle.

Figure 4:
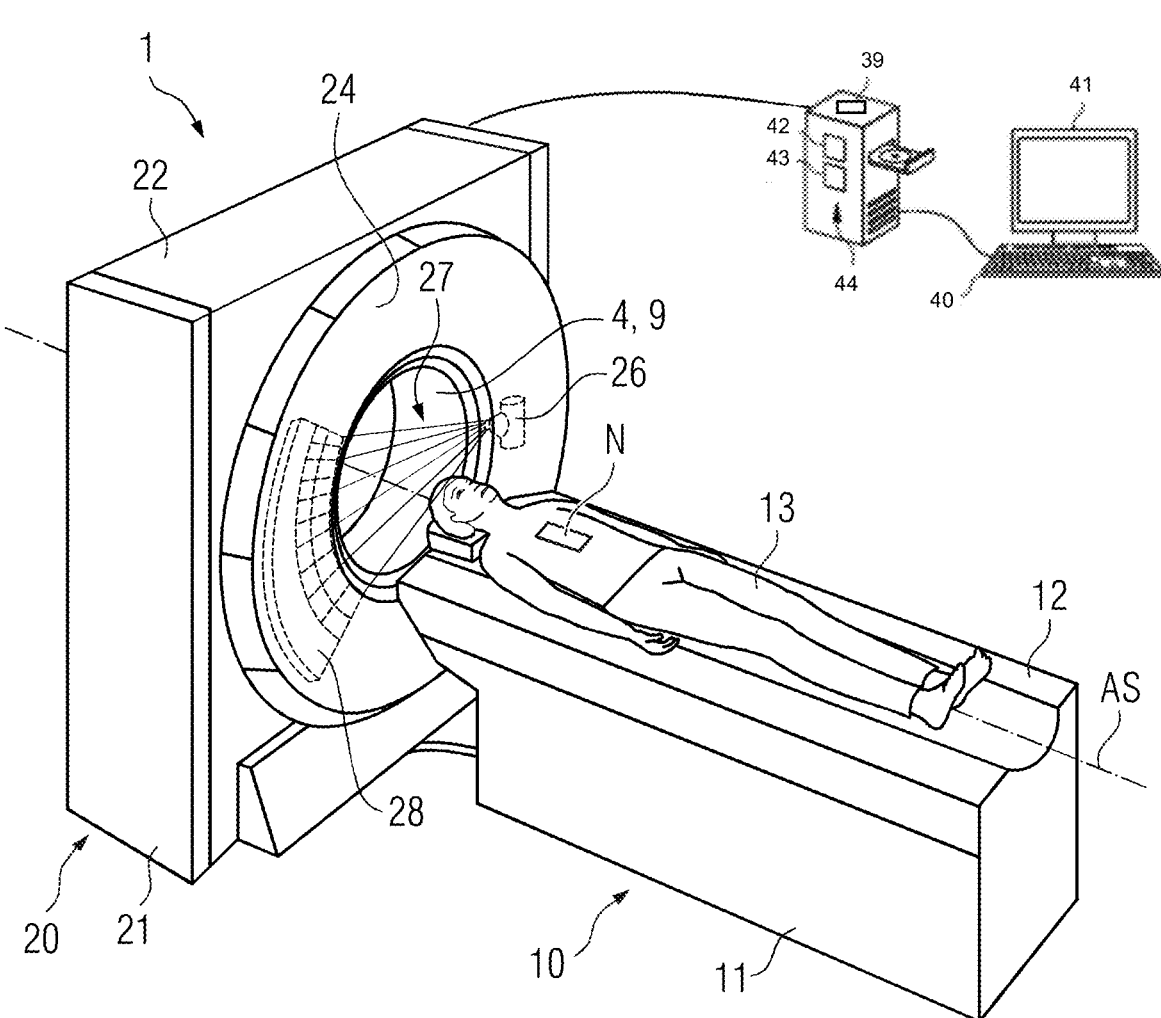
FIG. 4 shows a medical imaging device.

FIG. 4 shows the medical imaging device 1 in form of a computed tomography device, comprising the gantry 20, the support frame 21, the tilt frame 22, the rotor 24, the opening 9 for receiving the patient support structure 12, the radiological interaction area 4, the radiological interaction area 4 being located within the opening 9, the radiation source 26 for generating the x-ray fan 27 and the radiation detector 28. The medical imaging device 1 further comprises the patient table 10, the patient table 10 comprising the patient table socket 11 and the patient support structure 12 in the form of a patient table board. The patient table structure 12 is movably mounted on the patient table socket 11 along the system axis AS of the radiological interaction area 4. The patient 13 is located on the patient support structure 14.

The medical imaging device 1 comprises a data processing system 44, the data processing system 44 comprising a data interface 42 and a processor 43, the data processing system 44 being configured for carrying out the method for providing adapted 4D CT data. For example, the processor 43 is configured to execute instructions to cause the medical imaging device 1 to perform methods according to example embodiments. The data processing system 44 may further include a storage medium (computer-readable) 39 to store the instructions, an input device 40 and an output device 41. The input device 40 and the output device 41 can for example facilitate an interaction by a user or enable the visualization of a 4D CT scan. The medical imaging device 1 is configured for carrying out the first 4D CT scan relating to the anatomical structure N to obtain the initial 4D CT data and for carrying out the partial 4D CT scan relating to the anatomical structure N to obtain the supplementary 4D CT data.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor;

however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects.

Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A computer-implemented method for providing adapted 4D CT data, the method comprising:
   receiving initial 4D CT data, the initial 4D CT data corresponding to a first 4D CT scan, the first 4D CT scan relating to an anatomical structure on a first examination date;
   receiving supplementary 4D CT data, the supplementary 4D CT data corresponding to a partial 4D CT scan, the partial 4D CT scan relating to the anatomical structure on a second examination date;
   calculating the adapted 4D CT data based on the initial 4D CT data and the supplementary 4D CT data, the adapted 4D CT data corresponding to a second 4D CT scan, the second 4D CT scan relating to the anatomical structure on the second examination date; and
   providing the adapted 4D CT data.

2. The method of claim 1, wherein a radiation dose is reduced for the partial 4D CT scan compared to the first 4D CT scan.

3. The method of claim 1, wherein a scanned volume fraction of the anatomical structure is reduced for the partial 4D CT scan compared to the first 4D CT scan.

4. The method of claim 1, wherein
   a scan range of the partial 4D CT scan is selected based on the initial 4D CT data, and
   the scan range of the partial 4D CT scan is reduced compared to a scan range of the first 4D CT scan.

5. The method of claim 1, wherein an extent of an irradiation field along an x-ray fan direction is reduced for the partial 4D CT scan compared to the first 4D CT scan.

6. The method of claim 1, wherein a scanned fraction of a breathing cycle is reduced for the partial 4D CT scan compared to the first 4D CT scan.

7. The method of claim 6, wherein the calculating calculates the adapted 4D CT data based on the initial 4D CT data and the supplementary 4D CT data by applying an image registration from a given phase of the breathing cycle scanned during the first 4D CT scan to a corresponding phase in a part of the breathing cycle that was skipped during the partial 4D CT scan.

8. The method of claim 1, wherein the partial 4D CT scan is a prospective phase selective 4D CT scan of a single phase of a breathing cycle.

9. The method of claim 1, wherein
   a motion vector field of a breathing motion of the anatomical structure is calculated based on the initial 4D CT data, and
   the adapted 4D CT data is calculated based on the motion vector field and the supplementary 4D CT data.

10. The method of claim 1, wherein at least one of
    initial radiation treatment planning data regarding the anatomical structure is calculated based on the initial 4D CT data, or
    adapted radiation treatment planning data regarding the anatomical structure is calculated based on the adapted 4D CT data.

11. A non-transitory computer-readable storage medium, comprising instructions which, when executed by a computer, cause the computer to perform the method of claim 1.

12. A data processing system, comprising:
    a data interface; and
    a processor, the data processing system being configured to perform the method of claim 1.

13. A medical imaging device, comprising:
    the data processing system of claim 12, the medical imaging device being configured to at least one of,
        perform the first 4D CT scan relating to the anatomical structure to obtain the initial 4D CT data, or perform the partial 4D CT scan relating to the anatomical structure to obtain the supplementary 4D CT data.

14. The medical imaging device of claim 13, wherein the medical imaging device is at least one of a computed tomography device or a cone beam CT device.

15. A radiation treatment planning system, comprising:

the data processing system of claim 12, the radiation treatment planning system being configured to at least one of, provide initial radiation treatment planning data regarding the anatomical structure, or provide adapted radiation treatment planning data regarding the anatomical structure.

16. The method of claim 2, wherein a scanned volume fraction of the anatomical structure is reduced for the partial 4D CT scan compared to the first 4D CT scan.

17. The method of claim 16, wherein a scan range of the partial 4D CT scan is selected based on the initial 4D CT data, and the scan range of the partial 4D CT scan is reduced compared to a scan range of the first 4D CT scan.

18. The method of claim 17, wherein an extent of an irradiation field along an x-ray fan direction is reduced for the partial 4D CT scan compared to the first 4D CT scan.

19. The method of claim 18, wherein a scanned fraction of a breathing cycle is reduced for the partial 4D CT scan compared to the first 4D CT scan.

20. The method of claim 1, wherein the second 4D CT scan is different than the first 4D CT scan with respect to at least one of, a radiation dose, a scanned volume fraction of the anatomical structure, a scan range, an extent of an irradiation field along an x-ray fan direction, or a scanned fraction of a breathing cycle, wherein the second examination date occurs at least one day after the first examination date.

* * * * *